US005700904A

United States Patent [19]
Baker et al.

[11] Patent Number: 5,700,904
[45] Date of Patent: Dec. 23, 1997

[54] PREPARATION OF AN ACYLATED PROTEIN POWDER

[75] Inventors: Jeffrey Clayton Baker; Brian A. Moser; Warren E. Shrader, all of Indianapolis, Ind.

[73] Assignee: Eli Lilly and Company, Indianapolis, Ind.

[21] Appl. No.: 484,220

[22] Filed: Jun. 7, 1995

[51] Int. Cl.$^6$ .............................. C07K 1/30; C07K 1/36; C07K 14/62
[52] U.S. Cl. .................... 530/305; 530/344; 530/345; 530/410; 530/419
[58] Field of Search .................. 530/303, 305, 530/344, 417, 410, 345, 419; 514/3, 4, 21

[56] References Cited

U.S. PATENT DOCUMENTS

| | | | |
|---|---|---|---|
| 3,471,464 | 10/1969 | Bellet | 530/303 |
| 3,528,960 | 9/1970 | Haas | 530/303 |
| 3,591,574 | 7/1971 | Fenichel | 530/303 |
| 3,752,798 | 8/1973 | Amird | 530/303 |
| 3,755,569 | 8/1973 | Fenichel | 314/4 |
| 3,823,125 | 7/1974 | Grant | 530/303 |
| 3,843,815 | 10/1974 | Reesman | 426/325 |
| 3,864,325 | 2/1975 | Smyth | 530/303 |
| 3,868,356 | 2/1975 | Smyth | 530/303 |
| 3,868,357 | 2/1975 | Smyth et al. | 530/305 |
| 3,869,437 | 3/1975 | Lindsay | 530/303 |
| 3,883,496 | 5/1975 | Geiger | 530/303 |
| 3,883,500 | 5/1975 | Geiger et al. | 530/303 |
| 3,884,897 | 5/1975 | Geiger et al. | 530/303 |
| 3,950,517 | 4/1976 | Lindsay et al. | 514/3 |
| 4,013,628 | 3/1977 | Obermeier | 530/303 |
| 4,014,861 | 3/1977 | Geiger et al. | 530/303 |
| 4,486,458 | 12/1984 | Bradford et al. | 426/618 |
| 5,304,473 | 4/1994 | Belagaje | 435/69.7 |

FOREIGN PATENT DOCUMENTS

| | | |
|---|---|---|
| 214 826 A2 | 8/1986 | European Pat. Off. . |
| 383 472 A2 | 2/1990 | European Pat. Off. . |
| 1-254699 | 11/1989 | Japan . |
| 1260963 | 1/1972 | United Kingdom . |
| 1415333 | 11/1975 | United Kingdom . |
| 1492997 | 11/1977 | United Kingdom . |
| WO 92/01476 | 2/1992 | WIPO . |

OTHER PUBLICATIONS

Anderson, et al., "The Use of Esters of N–Hydroxysuccinimide in Peptide Synthesis," *Journal of American Chemical Society*, 86:1839–1842 (1964).
Asada, et al., "Stability of Acyl Derivatives of Insulin in the Small Intestine: Relative Importance of Insulin Association Characteristics in Aqueous Solution," *Pharmaceutical Research*, 11(8):1115–1120 (1994).
Geiger, et al., "Contribution of Peptide Chemistry to our Knowledge of Insulin and Diabetes," from *Proceedings of the Symposium on Proinsulin, Insulin and C–Peptide*, Tokushima, Jul. 12–14, pp. 62–72 (1978).
Geiger, et al, "Biological Activity of Insulin Analogues Substituted at the Amino Group of B1–Phenylalanine", from *Proceedings of the Second International Insulin Symposium*, Aachen, Germany, Sep. 4–7, pp. 409–415, (1979).
Geiger, "Chemie des Insulins," *Sonderdruck* 100:111–129, (1976) (Translation Attached).
Hashimoto, et al., "Synthesis of Palmitoyl Derivatives of Insulin and Their Biological Activities," *Pharmaceutical Research*, 6(2):171–176 (1989).
Hashizume, et al., "Improvement of Large Intestinal Absorption of Insulin by Chemical Modification with Palmitic Acid in Rats," *J. Pharm. Pharmacol.*, 44:555–559 (1992).
Inoue, et al., "Synthesis of a Superoxide Dismutase Derivative That Circulates Bound to Albumin and Accumulates in Tissues Whose pH is Decreased," *Biochemistry*, 28(16):6619–6624 (1989).
Kunitomo, et al., "Synthesis of Cytochrome c Derivative with Prolonged In Vivo Half–life and Determination of Ascorbyl Radicals in the Circulation of the Rat," *The Journal of Biological Chemistry*, 267(13):8732–8738 (1992).
Lapidot et al., "Use of Esters of N–hydroxysuccinimide in the Synthesis of N–acylamino Acids," *Journal of Lipid Research*, 11(8):1115–1120 (1994).
Lindsay et al., "Acetoacetylation of Insulin," *Biochem. J.*, 115:587–595 (1969).
Lindsay et al., "The Acetylation of Insulin," *Biochem. J.*, 121:737–745 (1971).
MacIntyre et al., "Information About Insulin by Chemical and Enzymatic Modifications," *Molecular Endocrinology*, Proceedings of Endocrinology '77 held at the Royal College of Physicians, London, England Jul. 11–15, pp. 27–42 (1977).
Muranishi, et al., "Trials of Lipid Modification of Peptide Hormones for Intestinal Delivery," *Journal of Controlled Release*, 19:179–188 (1992).
Riordan, et al., "Acetylation," *Methods of Enzymology*, 25:494–499 (1972).
Roösen et al., "A1–Modified Insulins: Receptor Binding and Biological Activity," Insulin Chemistry, Structure and Function of Insulin and Related Hormones from Proceedings of the Second International Insulin Symposium, Aachen, Germany, Sep. 4–7, pp. 403–408 (1979).
Scheider, "Ligand–Independent Activated State of Serum Albumin for Fatty Acid Binding," *Journal of Physical Chemistry*, 84(8):925–928 (1980).
Harris, E. L. V. and Angal, S. Protein Purification Methods: a Practical Approach. Oxford: Oxford University Press. 1989, pp. 152–160.

*Primary Examiner*—Jeffrey E. Russel
*Attorney, Agent, or Firm*—Steven P. Caltrider

[57] ABSTRACT

A method for recovering an acylated protein as a powder, especially in cases where said acylated protein is one that resists isolation by isoelectric precipitation from aqueous solutions of the protein, said method comprising in combination adjusting said aqueous solution to near the isoelectric pH of the protein and providing a suitable alcohol concentration to cause precipitation of the protein in the form of filterable particles at said pH.

15 Claims, No Drawings

000000# PREPARATION OF AN ACYLATED PROTEIN POWDER

BACKGROUND OF THE INVENTION

1. Field of the Invention

The present invention is broadly directed to a method for recovering, as a powder, an acylated protein, particulary those that resist recovery by precipitation or crystallization and subsequent filtration from aqueous solutions, and especially certain acylated proinsulins, acylated insulins or acylated insulin analogs. More particularly, the present invention relates to the preparation of a freely-flowing powder of certain acylated proinsulins, insulins and insulin analogs from their aqueous solutions.

2. Description of Related Art

It has long been a goal of insulin therapy to mimic the pattern of endogenous insulin secretion in normal individuals. The daily physiological demand for insulin fluctuates and can be separated into two phases: (a) the absorptive phase requiring a pulse of insulin to dispose of the meal-related blood glucose surge, and (b) the post-absorptive phase requiring a sustained amount of insulin to regulate hepatic glucose output for maintaining optimal fasting blood glucose. Accordingly, effective therapy generally involves the combined use of two exogenous insulins: a fast-acting meal time insulin provided by bolus injections and a long-acting basal insulin administered by injection once or twice daily.

Recently, a class of acylated insulins has shown promise for use as a long-acting basal insulin therapy. These acylated insulins are prepared by acylating, selectively with an activated fatty acid derivative, the free amino group(s) of a monomeric insulin, including a proinsulin, normal insulin and certain insulin analogs. Useful fatty acid derivatives include reactive fatty acid-type compounds having at least a six (6) carbon atom chain length and particularly those fatty acid derivatives having 8 to 21 carbon atoms in their chain. Mono-acylated normal human insulin, acylated with a palmitic acid derivative, is a particularly promising candidate. Insulins falling within this catagory are described in Japanese patent application 1-254,699.

As well-understood by those skilled in this art, ways of recovering a protein in a solid, preferably free-flowing powder, form is especially advantageous, if not essential, in many applications. Preparation of a protein as a powder, for example, maximizes storage and distribution options. This is particularly true in the context of compositions destined for insulin therapy where high volumes of product must be produced to satisfy demand. Fortuitously, it was long ago discovered that normal insulin, including beef insulin, pork insulin and human insulin, could be recovered as a powder by precipitation, or more accurately crystallization, of the insulin from relatively dilute aqueous insulin solutions as a zinc complex or as sodium crystals. In general, so-called zinc insulin is crystallized from a buffered aqueous solution containing zinc ions and can readily be isolated by filtration.

Unfortunately, attempts to recover insulins acylated with long chain fatty acid derivatives by filtration have not been as successful. Indeed, known attempts to crystallize fatty acid-acylated insulins have been uniformly unsuccessful. It has been postulated that the hydrophobic character of the long chain fatty acid moiety on such insulin monomers contributes to this difficulty by interfering inter alia with the protein-protein interactions required for satisfactory crystal formation. Consequently, other ways must be found for preparing these acylated insulins in a solid, powdered form.

One technically feasible approach to produce an acylated protein, such as an acylated insulin, in a powdered form is to lyophilize an aqueous solution of the protein. While powdered preparations of fatty acid-acylated insulins can be produced in this way, lyophilization techniques are not conveniently adapted to production of the large quantities of insulin needed commercially. Issues of operator safety and product handling are particularly problematic for large volume lyophilization operations.

Another potential strategy involves isoelectric precipitation. Proteins in an aqueous solution have long been known to become less soluble as the pH of the environment is adjusted to near the protein's isoelectric point. This general phenomenon has long been exploited in protein purification and recovery processes. Once insolubilized, such proteins often can be recovered from the resulting aqueous suspension by simple gravity thickening or by vacuum-assisted and pressure-assisted filtration.

Unfortunately, our attempts to recover fatty acid-acylated insulins simply by adjusting the pH of an aqueous solution of the acylated protein to near its isoelectric point has produced emulsion-like compositions that resist easy solid-liquid separation, such as by gravity thickening or vacuum-assisted and pressure-assisted filtration. As a result, a new approach for recovering such acylated insulin species in a powder form must be found.

The present invention provides a simple procedure for recovering acylated proteins by precipitation and fitration as a freely-flowing powder, and especially certain fatty acid-acylated insulins that resist such isolation and recovery by precipitation and filtraton. The present invention thus provides a method for recovering fatty acid-acylated insulins as a freely-flowing powder from aqueous solutions. In particular, the present invention provides a process for recovering a powdered, fatty acid-acylated insulin that can be adapted conveniently to relatively large scale production techniques. The present invention also pertains to the powdered protein prepared by this method.

DESCRIPTION OF THE INVENTION

All amino acid abbreviations used in this disclosure are those accepted by the United States Patent and Trademark Office as set forth in 37 C.F.R. § 1.822(B)(2).

The terms "insulin" and "normal insulin" as used herein mean human insulin, pork insulin, or beef insulin. Insulin possesses three free amino groups: $B^1$-Phenylalanine, $A^1$-Glycine, and $B^{29}$-Lysine. The free amino groups at positions $A^1$ and $B^1$ are α-amino groups. The free amino group at position $B^{29}$ is an ε-amino group.

The term "proinsulin" as used herein is a properly cross-linked protein of the formula:

B—C—A wherein:

A is the A chain of insulin or a functional derivative thereof;

B is the B chain of insulin or a functional derivative thereof having an ε-amino group; and C is the connecting peptide of proinsulin. Preferably, proinsulin is the A chain of human insulin, the B chain of human insulin, and C is the natural connecting peptide. When proinsulin is the natural sequence, proinsulin possesses three free amino groups: Phenylalanine(1) (α-amino group), Lysine(29) (ε-amino group) and Lysine(64) (ε-amino group).

The term "insulin analog" as used herein is a properly cross-linked protein exhibiting insulin activity of the formula:

A–B wherein:

A is the A chain of insulin or a functional derivative of the insulin A chain; and B is the B chain of insulin or a functional derivative of the insulin B chain having an ε-amino group and at least one of A or B contains an amino acid modification from the natural sequence.

Preferred insulin analogs include insulin wherein:

the amino acid residue at position $B^{28}$ is Asp, Lys, Leu, Val, or Ala;

the amino acid residue at position $B^{29}$ is Lys or Pro;

the amino acid residue at position $B^{10}$ is His or Asp;

the amino acid residue at position $B^1$ is Phe, Asp, or deleted alone or in combination with a deletion of the residue at position $B^2$;

the amino acid residue at position $B^{30}$ is Thr, Ala, or deleted; and the amino acid residue at position $B^9$ is Ser or Asp; provided that either position $B^{28}$ or $B^{29}$ is Lys.

In standard biochemical terms known to the ordinarily skilled artisan the preferred insulin analogs are $Lys^{B28}Pro^{B29}$-human insulin ($B^{28}$ is Lys; $B^{29}$ is Pro); $Asp^{B28}$-human insulin ($B^{28}$ is Asp); $Asp^{B1}$-human insulin, $Arg^{B31,B32}$-human insulin, $Asp^{B10}$-human insulin, $Arg^{A0}$-human insulin, $Asp^{B1}$,$Glu^{B13}$-human insulin, $Ala^{B26}$-human insulin, and $Gly^{A21}$-human insulin.

The term "acylating" means the introduction of one or more acyl groups covalently bonded to the free amino groups of the protein.

The term "fatty acid" means a saturated or unsaturated $C_6$–$C_{21}$ fatty acid. The term "activated fatty acid ester" means a fatty acid which has been activated using general techniques such as described in *Methods of Enzymology*, 25:494–499 (1972) and Lapidot et al., in *J. of Lipid Res.*, 8:142–145 (1967), the disclosures of which are incorporated herein by reference. The preferred fatty acids are saturated and include myristic acid ($C_{14}$), pentadecylic acid ($C_{15}$), palmitic acid ($C_{16}$) heptadecylic acid ($C_{17}$) and stearic acid ($C_{18}$). Most preferably, the fatty acid is palmitic acid. Activated fatty acid esters include derivatives of agents such as hydroxybenzotriazide (HOBT), N-hydroxysuccinimide and derivatives thereof. The preferred activated ester is N-succinimidyl palmitate.

The term "cross-link" means the formation of disulfide bonds between cysteine residues. A properly cross-linked proinsulin, insulin or insulin analog contains three disulfide bridges. The first disulfide bridge is formed between the cysteine residues at positions 6 and 11 of the A-chain. The second disulfide bridge links the cysteine residues at position 7 of the A-chain to the cysteine at position 7 of the B-chain. The third disulfide bridge links the cysteine at position 20 of the A-chain to the cysteine at position 19 of the B-chain.

The term "precipitation" refers to a process in which readily filterable particles are produced in a liquid and is to be distinguished from simply a change in the solubility of a solute in solution leading to the formation of stable suspensions and/or emulsion-like, two phase mixtures. The filterable particles themselves are referred to as a "precipitate".

The phrase "readily filterable" and other similar phrases refers to a condition in which the particles of a solid-liquid mixture or slurry can be isolated by a process of dead-end filtration and related techniques to a handleable filter cake, i.e. a material with a residual moisture content that does not interfere with the handling of the cake as a solid rather than a slurry. In "dead-end" filtration, the slurry is delivered and filtrate liquid passes substantially perpendicular to the plane of the filter and is to be contrasted with "crossflow" or "tangential-flow" filtration in which the main liquid flow is parallel to the surface of the filter medium. Importantly, the method of the present invention produces a slurry of an acylated protein that can be isolated by dead-end filtration and related techniques at an average or mean filtration rate exceeding 5 $l/m^2/hr$ (LMH), and often at an average or mean filtration rate greater than 20 LMH, the endpoint of the filtration normally being the point when the cake can be handled as a solid. Such filtration rates are critical for economy of operation on a commercial production scale.

The term "aqueous" includes cosolvent systems as well as use of water only as a solvent.

The present invention relates to a method for recovering an acylated protein as a powder from an aqueous mixture, especially those acylated proteins that resist isolation and recovery by isoelectric precipitation from an aqueous solution of the acylated protein. The method comprises adjusting an aqueous solution of the acylated protein to a pH that causes the protein in solution to become insoluble and adding sufficient alcohol to the aqueous mixture of the protein to cause precipitation of the protein in the form of filterable particles at said pH.

In another aspect, the present invention pertains to a powdered acylated protein, particularly an acylated protein that resists isolation by isoelectric precipitation from an aqueous solution. In particular, the present invention pertains to a fatty acid-acylated proinsulin, a fatty acid-acylated insulin or a fatty acid-acylated insulin analog in the form of a powder, prepared by adjusting an aqueous solution of the acylated insulin protein to a pH that causes the protein in said aqueous solution to become insoluble, and adding sufficient alcohol to the aqueous protein to cause precipitation of the protein in the form of filterable particles at said pH. Thereafter, the protein can be recovered as a zinc-free powdered acylated protein by filtration and drying. Preferred acylated proteins prepared in powder form using the method of the present include N-palmitoyl $Lys^{B29}$ human insulin and B28-$N^\epsilon$-palmitoyl-$Lys^{B28}Pro^{B29}$-human insulin (B28 is acylated Lys and B29 is Pro).

Proinsulin, insulin and insulin analogs used to prepare the acylated proteins that are the principal focus of the present invention can be prepared by any of a variety of recognized peptide synthesis techniques including classical (solution) methods, solid phase methods, semi-synthetic methods, and more recent recombinant DNA methods. For example, Chance et al., U.S. patent application Ser. No. 07/388,201, now abandoned EPO publication number 383 472, Brange et al., EPO 214 826, and Belagaje et al., U.S. Pat. No. 5,304,473 disclose the preparation of various proinsulin and insulin analogs and are herein incorporated by reference. The A and B chains of the insulin analogs of the present invention may also be prepared via a proinsulin-like precursor molecule using recombinant DNA techniques. See Frank et al., Peptides: Synthesis-Structure-Function, *Proc. Seventh Am. Pept. Symp.*, Eds. D. Rich and E. Gross (1981) which is incorporated herein by reference.

Generally, the proinsulin, insulin and insulin analogs are acylated by reacting them with an activated fatty acid derivative, such as an activated fatty acid ester. The acylation of normal insulin with a fatty acid is disclosed in Japanese patent application 1-254,699. See also Hashimoto et al., *Pharmaceutical Research*, 6:171–176 (1989). These disclosures are incorporated herein by reference.

Preferably, the acylation is conducted under basic conditions, i.e., at a pH greater than 9.0 and preferably about 10.5, in a polar solvent. While the reaction can be conducted in a wholly organic polar solvent using a base having an aqueous pKa of greater than or equal to 10.75, we prefer a mixed organic and aqueous solvent for the reaction medium. Preferred bases are tetramethylguanidine, diisopropylethylamine or tetrabutylammonium hydroxide. One particularly suitable solvent has been acetonitrile and water, containing about 50% acetonitrile. Other polar solvents include dimethylsulfoxide, dimethylformamide and the like. Cosolvent systems also include acetone and water, isopropyl alcohol and water, and ethanol and water. Time and temperature conditions suitable for conducting the reactions are not narrowly critical. A temperature of 0° to 40° C. and a reaction time of 15 minutes to 24 hours should generally be suitable. A particularly preferred way of preparing such fatty acid-acylated insulins is described in copending U.S. application Ser. No. 08/341231 filed Nov. 17, 1994, the disclosure of which is incorporated herein by reference.

Once the reaction is complete, the reaction mixture containing the acylated protein typically is diluted with water and an acid is added to neutralize the alkalinity. The acid is supplied as an aqueous solution to the acylated protein and serves to lower the solution pH to below the isoelectric point of the protein. Normally, at this point the protein is in a properly buffered aqueous solution for further processing. Such processing particularly includes purification by standard chromatographic methods such as reverse phase or hydrophobic chromatography, concentration by crossflow filtration, solvent exchange by ultrafiltration and the like. For acylated proinsulin, acylated insulin and acylated insulin analogs, particularly N-palmitoyl $Lys^{B29}$ human insulin and B28-$N^{\epsilon}$-palmitoyl-$Lys^{B28}Pro^{B29}$-human insulin, the pH normally should be adjusted to below about 3.0, and preferably to between about 1.5 and 2.5, using the acid as needed. Suitable acids include HCl, acetic acid, glycine and especially citric acid. Use of citric acid at a concentration of 50 mM has been found suitable. If needed the pH also can be readjusted with a base, such as sodium hydroxide, to keep it within the desired range.

At this point, the aqueous solution of the isolated, and preferably purified acylated protein, particularly a fatty acid-acylated proinsulin, a fatty acid-acylated insulin or a fatty acid-acylated insulin analog, can be processed in accordance with the present invention to recover the soluble protein as a powder. According to the invention, the pH of the aqueous protein solution is adjusted, by the addition of a base, preferably a water-soluble base such as sodium hydroxide, in a sufficient amount to cause the soluble protein to become insoluble. This is accomplished by adjusting the solution pH to near the isoelectric point of the acylated protein, alternatively referred to as the isoelectric pH. In the case of a fatty acid-acylated proinsulin, a fatty acid-acylated insulin and a fatty acid-acylated insulin analog, particularly N-palmitoyl $Lys^{B29}$ human insulin, adjustment of the pH to within the range of about 4.0 to 6.0, and preferably to about 4.5 to 5.5 has proven suitable. At this pH, the net charge on the acylated protein should be at a minimum and the solubility of the protein should be at its lowest. During adjustment of the pH, the solution should be agitated to obtain complete mixing.

Aqueous solutions of the acylated proteins, which are especially amenable for treatment in accordance with the present invention, form an emulsion-like composition when the pH is adjusted to near their isoelectric pH. This condition interferes with isolation of the protein using those solid/liquid separation techniques, such as deadend filtration, desireable for large scale processing. A key feature of the present invention relates to the use of an alcohol, especially ethanol, added to the aqueous protein mixture to assist the formation of an easily filterable precipitate of the acylated protein.

The sequence for adjusting the solution pH and adding the alcohol is not critical. The alcohol can be added to the protein solution prior to the pH adjustment required for protein insolubilization and eventual precipitate formation and also can be added after the pH adjustment of the protein solution.

Applicants have found that the amount of alcohol that must be added to the acylated protein to obtain an easily filterable precipitate falls within a narrow range. In particular, applicants have discovered that for a fatty acid-acylated insulin, and especially N-palmitoyl $Lys^{B29}$ human insulin, the desired result, i.e., formation of an easily filtered precipitate, is obtained only upon adding an amount of alcohol, especially ethanol, in a narrow range to provide a final alcohol concentration of at least about 20% and up to about 35%, and preferably about 25% to 30%, in the aqueous protein suspension or slurry. While ethanol is clearly the alcohol of choice, other alcohols such as methanol and isopropanol should be suitable substitutes in certain circumstances.

Adding too much alcohol to the aqueous protein interferes with obtaining an acceptable level of precipitate formation, while adding an insufficient amount does not adequately resolve the emulsion-like composition produced upon pH adjustment of the acylated protein into a readily filterable slurry or suspension. Indeed, at higher than desired levels of the alcohol, the protein will redissolve contributing to possible reductions in yield. Determining an amount of alcohol, such as ethanol, needed to facilitate precipitation and filtration of other fatty acid-acylated proteins can be done using routine experimentation.

In effect, therefore, the invention is based on the recognition that to recover, as a freely-flowing powder, an acylated protein particularly one that otherwise resists isolation and recovery by isoelectric precipitation and filtration from aqueous solutions of the protein, one must produce the following combination of conditions, (a) a pH at or near the isoelectric pH of the protein and (b) a sufficient alcohol concentration to assist precipitation and filtration of the protein by facilitating the formation of easily filterable particles. As noted above, in the case of N-palmitoyl $Lys^{B29}$ human insulin, an ethanol concentration of about 20% to 35% by volume of slurry, and preferably 25% to 30% by volume, has been found to be particularly suitable to assist precipitation of the protein in the form of readily filterable particles.

The method by which an aqueous protein mixture is prepared broadly to have the required alcohol (e.g. ethanol) concentration and to exhibit the isoelectric pH of the acylated protein is not critical. For example, such a mixture can be obtained by diluting, with water, a pH-adjusted aqueous solution of the protein having a higher than required alcohol concentration, i.e. in the case of N-palmitoyl $Lys^{B29}$ human insulin by diluting an ethanol concentration of above 35% by volume, i.e. from 40 to 45% ethanol, to an alcohol concentration in the desired range. Preferably, the composition is gently stirred (mixed) at the point both the alcohol concentration and the pH are within desired limits to facilitate precipitate formation.

The concentration of the acylated protein in the solution prior to treatment in accordance with the present invention also is not critical. In the case of acylated insulins, including also acylated proinsulin and acylated insulin analogs, a concentration of at least about 1 mg/ml, and preferably at least about 5 mg/ml, generally should be used, though using a protein concentration as high as 35 to 50 mg/ml and higher should provide a precipitated protein that can be processed at more acceptable filtration rates. As noted above, the protein slurry produced by the combined treatment of pH adjustment and alcohol addition should exhibit an average or mean filtration rate of at least about 5 LMH, and preferably exhibits a mean filtration rate of at least about 15 LMH. Surprisingly, mean filtration rates of about 20 LMH and higher have been observed upon treating N-palmitoyl Lys$^{B29}$ human insulin solutions in accordance with the present invention.

Although not narrowly critical, for best results, the temperature during the filtration is kept in the range of 20° C. to 30° C. Temperatures of 0° C. or below, however, should be avoided during filtration as such temperatures interfere with operation at the desired high filtration rates. While the filtration preferably is done at essentially ambient temperatures, the prior pH adjustment and ethanol addition steps can be done at any temperature above the freezing point of the slurry.

At this point, the aqueous protein composition is ready to be filtered to isolate the precipitated protein. In some cases, it may be advantageous to perform a gravity thickening or settling of the aqueous protein composition or slurry before the filtration in order to minimize the hydraulic load on the filtation equipment. While centrifugal filtration of the aqueous protein composition may be advantageous at larger treatment scales, e.g. production batches of greater than about 0.5 kg, any means for liquid/solid separation, including vacuum-assisted or pressure-assisted filtration, can be used to recover the precipitated protein in the broad practice of the present invention. On a smaller scale, e.g. batch sizes below about 0.3 to 0.5 kg, pressure-assisted filtration using a filtration device having a porous frit filtration surface can be used with advantage. Filtration through a porous frit with about 5.0 μm nominal pore size has proven quite effective. The equipment used to filter the slurry is not narrowly critical and any of the wide variety of known filtration systems compatible with the processing of pharmaceutical compositions can be used.

Following filtration, the filter cake is recovered and dried, generally by vacuum-assisted evaporation. In the broad practice of the present invention, any method for drying a thickened paste of solids, not otherwise injurious to the isolated protein, can be used. Ways for recovering the filter cake and other ways for drying the filter cake should be apparent to those skilled in the art and are not critical.

The acylated insulin powders of the present invention are useful as a bulk drug substance (BDS) for preparing pharmaceutical compositions used in insulin therapy, i.e. for administering to a patient in need thereof (i.e. a patient suffering from hyperglycemia). Such pharmaceutical compositions contain an effective amount of the powder in combination with one or more pharmaceutically acceptable excipients or carriers. For these purposes, the pharmaceutical compositions may typically be formulated so as to contain about 100 units per mL or similar concentrations containing an effective amount of the acylated insulin powder. These compositions are typically, though not necessarily, parenteral in nature and may be prepared by any of a variety of techniques using conventional excipients or carriers for parenteral products which are well known in the art. See, for example, *Remington's Pharmaceutical Sciences*, 17th Edition, Mack Publishing Company, Easton, Pa., USA (1985) which is incorporated herein by reference. For example, dosage forms for parenteral administration may be prepared by suspending or dissolving the desired amount of the protein powder in a non-toxic liquid vehicle suitable for injection such as an aqueous medium and sterilizing the suspension or solution. Alternatively, a measured amount of the powder may be placed in a vial; and the vial and its contents sterilized and sealed. An accompanying vial or vehicle can be provided for purposes of mixing prior to administration.

Pharmaceutical compositions adapted for parenteral administration employ diluents, excipients and carders such as water and water-miscible organic solvents such as glycerin, sesame oil, groundnut oil, aqueous propylene glycol, N,N-dimethylformamide and the like. Examples of such pharmaceutical compositions include sterile, isotonic, aqueous saline solutions of the powder that can be buffered with a pharmaceutically acceptable buffer and that are pyrogen free. Additionally, the parenteral pharmaceutical formulation may contain preservatives such as metacresol, other agents to adjust pH of the final product such as sodium hydroxide or hydrochloric acid and stabilizers such as zinc salts.

The following example is presented to illustrate and explain the invention. While the invention is illustrated by reference to the recovery of N-palmitoyl Lys$^{B29}$ humin insulin as a powder, the scope of the invention should not be consisdered as being limited to this example. Unless otherwise indicated, all references to parts and percentages are based on weight and all temperatures are expressed in degrees Celsius.

EXAMPLE

An aqueous solution (8.8 l) of a fatty acid-acylated Biosynthetic Human Insulin (N-palmitoyl Lys$^{B29}$ human insulin), having a protein concentration of 50 mg/ml and at a pH of 2.6, is treated at a temperature of 2°–8° C. with 530 ml of 10% sodium hydroxide which increases the pH to 5.7. Following agitation of the pH-adjusted solution to obtain thorough mixing, absolute ethanol, in an amount of 0.46 liter per liter of the pH-adjusted solution (to a total solution volume of 13 l), was added, with gentle stirring, to assist precipitation of the acylated insulin. The acylated protein slurry was dewatered on a pressure-assisted filter having a stainless steel frit, nominal 5.0 μ pore size. The observed mean filtration rate was about 25 LMH. The filtrate was discarded. The filter cake then was washed with an aqueous solution containing 30% ethanol by volume, and the washed filter cake was recovered from the filter and dried under a vacuum to yield a zinc-free powder. This powder has been observed to have excellent storage stability making it suitable as a pharmaceutical bulk drug substance. Substantially all of the protein was recovered in the filter cake with very little lost via the filtrate.

The principles, preferred embodiments and modes of operation of the present invention have been described with particularity in the foregoing specification primarily with reference to fatty acid-acylated proinsulin, insulin and insulin analogs, particulary N-palmitoyl Lys$^{B29}$ human insulin. The invention which is intended to be protected herein, however, is not to be construed as limited to the particular forms disclosed, since they are to be regarded as illustrative rather than restrictive. Variations and changes may be made by those skilled in the art without departing from the spirit of the invention as defined in the following claims.

We claim:

1. A process for forming a fatty acid-acylated protein precipitate, which comprises, adjusting the pH of a solution comprising the fatty acid-acylated protein and adding alcohol, such that the fatty acid-acylated protein precipitates.

2. The process of claim 1, wherein adjusting the pH precedes adding alcohol.

3. The process of claim 1, wherein adding alcohol precedes adjusting the pH.

4. The process of claim 1, wherein the fatty acid-acylated protein is selected from the group consisting of a fatty acid-acylated insulin, a fatty acid-acylated insulin analog, and a fatty acid-acylated proinsulin.

5. The process of claim 4, wherein the pH is adjusted to a pH between about 4.0 and about 6.0.

6. The process of claim 5, wherein the fatty acid-acylated protein is B29-$N^{\epsilon}$-fatty acid-acylated human insulin.

7. The process of claim 6, wherein the fatty acid-acylated protein is B29-$N^{\epsilon}$-palmitoyl-acylated human insulin.

8. The process of claim 6, wherein the fatty acid-acylated protein is B29-$N^{\epsilon}$-myristoyl-acylated human insulin.

9. The process of claim 5, wherein the fatty acid-acylated protein is B28-$N^{\epsilon}$-fatty acid-acylated Lys$^{B28}$, Pro$^{B29}$-human insulin.

10. The process of claim 9, wherein the fatty acid-acylated protein is B28-$N^{\epsilon}$-palmitoyl-acylated Lys$^{B28}$, Pro$^{B29}$-human insulin.

11. The process of claim 9, wherein the fatty acid-acylated protein is B28-$N^{\epsilon}$-myristoyl-acylated Lys$^{B28}$, Pro$^{B29}$-human insulin.

12. The process of claim 5, wherein the fatty acid-acylated protein is B1-$N^{\alpha}$-fatty acid-acylated human insulin.

13. The process of claim 5, wherein the fatty acid-acylated protein is B1-$N^{\alpha}$-fatty acid-acylated Lys$^{B28}$,Pro$^{B29}$-human insulin.

14. The process of claim 5, wherein the alcohol is ethanol, and wherein ethanol is added in an amount to yield a concentration of ethanol in the solution of about 20% to about 35% by volume.

15. A process for producing a fatty acid-acylated protein powder, which comprises, a) recovering the fatty acid-acylated protein precipitate produced by the process of claim 1; and b) drying the recovered precipitate of step a) to produce a powder comprising the fatty acid-acylated protein.

* * * * *